US00PP24708P2

(12) United States Plant Patent
Keogh

(10) Patent No.: US PP24,708 P2
(45) Date of Patent: Jul. 29, 2014

(54) ***EUPHORBIA* PLANT NAMED 'UNIEUP-1'**

(50) Latin Name: *Euphorbia graminea*
Varietal Denomination: UNIEUP-1

(75) Inventor: Terence Charles Keogh, Victoria Point (AU)

(73) Assignee: Amerinova Properties LLC, Bonsall, CA (US)

( * ) Notice: Subject to any disclaimer, the term of this patent is extended or adjusted under 35 U.S.C. 154(b) by 156 days.

(21) Appl. No.: 13/507,513

(22) Filed: Jul. 5, 2012

(51) Int. Cl.
*A01H 5/00* (2006.01)

(52) U.S. Cl.
USPC ..... Plt./302

(58) Field of Classification Search
CPC ..... A01H 5/02; A01H 5/0244
USPC ..... Plt./302
See application file for complete search history.

*Primary Examiner* — June Hwu
(74) *Attorney, Agent, or Firm* — C. A. Whealy

(57) ABSTRACT

A new and distinct cultivar of *Euphorbia* plant named 'UNIEUP-1', characterized by its compact, upright, outwardly spreading and mounding plant habit; vigorous growth habit; freely branching habit; and numerous white-colored flowers.

1 Drawing Sheet

Botanical designation: *Euphorbia graminea.*
Cultivar denomination: 'UNIEUP-1'.

BACKGROUND OF THE INVENTION

The present invention relates to a new and distinct cultivar of *Euphorbia* plant, botanically known as *Euphorbia graminea* and hereinafter referred to by the name 'UNIEUP-1'.

The new *Euphorbia* plant is a product of a planned breeding program conducted by the Inventor in Victoria Point, Queensland, Australia. The objective of the breeding program is to create new compact *Euphorbia* plants with numerous flowers.

The new *Euphorbia* plant originated from a self-pollination in April, 2008 in Victoria Point, Queensland, Australia of *Euphorbia graminea* 'Inneuphdia', disclosed in U.S. Plant Pat. No. 17,567. The new *Euphorbia* plant was discovered and selected by the Inventor as a single flowering plant within the progeny of the stated self-pollination in a controlled greenhouse environment in Victoria Point, Queensland, Australia in November, 2008.

Asexual reproduction of the new *Euphorbia* plant by vegetative cuttings in a controlled greenhouse environment in Victoria Point, Queensland, Australia since November, 2008, has shown that the unique features of this new *Euphorbia* plant are stable and reproduced true to type in successive generations.

SUMMARY OF THE INVENTION

Plants of the new *Euphorbia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'UNIEUP-1'. These characteristics in combination distinguish 'UNIEUP-1' as a new and distinct *Euphorbia* plant:

1. Compact, upright, outwardly spreading and mounding plant habit.
2. Vigorous growth habit.
3. Freely branching habit.
4. Numerous white-colored flowers.

The new *Euphorbia* can be compared to plants of the parent, 'Inneuphdia'. Plants of the new *Euphorbia* differ primarily from plants of 'Inneuphdia' in the following characteristics:

1. Plants of the new *Euphorbia* are more compact than plants of 'Inneuphdia'.
2. Plants of the new *Euphorbia* have shorter internodes than plants of 'Inneuphdia'.
3. Plants of the new *Euphorbia* have darker-colored lateral branches than plants of 'Inneuphdia'.
4. Plants of the new *Euphorbia* and 'Inneuphdia' differ slightly in flower color.

Plants of the new *Euphorbia* can be compared to plants of *Chamaesyce hypericifolia* 'Silverfog', disclosed in U.S. Plant Pat. No. 20,858. Plants of the new *Euphorbia* differ from plants of 'Silverfog' in the following characteristics:

1. Plants of the new *Euphorbia* are slightly more vigorous than plants of 'Silverfog'.
2. Plants of the new *Euphorbia* have darker-colored lateral branches than plants of 'Silverfog'.
3. Plants of the new *Euphorbia* and 'Silverfog' differ slightly in flower color.

BRIEF DESCRIPTION OF THE PHOTOGRAPHS

The accompanying colored photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the bottom of the sheet is a side perspective view of a typical flowering plant of 'UNIEUP-1' grown in a container.

The photograph at the top of the sheet is a close-up view of a typical flowering plant of 'UNIEUP-1'.

DETAILED BOTANICAL DESCRIPTION

The aforementioned photographs and following observations, measurements and values describe plants grown in 15.24-cm containers during the early spring in a polyethylene-covered greenhouse in Bonsall, Calif. and under cultural practices typical of commercial *Euphorbia* production. During the production of the plants, day temperatures ranged from 20° C. to 24° C., night temperatures ranged from 14° C. to 18° C. and light levels ranged from 4,200 to 5,000 lux. Plants were pinched two times and were four months old when the photographs and description were taken. In the following description, color references are made to The Royal Horticultural Society Colour Chart, 2007 Edition, except where general terms of ordinary dictionary significance are used.

Botanical classification: *Euphorbia graminea* 'UNIEUP-1'.

Parentage: Self-pollination of *Euphorbia graminea* 'Inneuphdia', disclosed in U.S. Plant Pat. No. 17,567.

Propagation:

*Type*.—By vegetative cuttings.

*Time to initiate roots, summer*.—About 14 days at temperatures of about 20° C.

*Time to initiate roots, winter*.—About 18 days at temperatures of about 20° C.

*Time to produce a rooted young plant, summer and winter*.—About 20 days at temperatures of about 20° C.

*Root description*.—Fine, fleshy; white in color.

*Rooting habit*.—Freely branching; medium density.

Plant description:

*Plant form and growth habit*.—Compact, upright, outwardly spreading and mounding plant habit; broad inverted triangle; vigorous growth habit.

*Branching habit*.—Freely branching habit; plants with numerous secondary and tertiary lateral branches developing per plant; pinching enhances lateral branch development.

*Plant height*.—About 14.5 cm.

*Plant diameter*.—About 28 cm.

*Lateral branch description*.—Length: About 12.5 cm. Diameter: About 1.5 mm. Internode length: About 4 cm. Strength: Moderately strong. Texture: Smooth, glabrous. Color: Close to 137B.

Foliage description:

*Arrangement*.—Opposite; simple.

*Length*.—About 1.1 cm.

*Width*.—About 6 mm.

*Shape*.—Elliptical.

*Apex*.—Broadly acute to slightly rounded.

*Base*.—Attenuate.

*Margin*.—Entire.

*Texture, upper surface*.—Mostly glabrous; few tiny hairs along the margins.

*Texture, lower surface*.—Pubescent.

*Venation*.—Pinnate, arcuate.

*Color*.—Developing leaves, upper surface: Close to 137A. Developing leaves, lower surface: Close to 137C. Fully developed leaves, upper surface: Close to 137A; venation, close to 137A. Fully developed leaves, lower surface: Close to 137B; venation, close to 138B.

*Petioles*.—Length: About 9 mm. Diameter: About 1 mm. Texture, upper and lower surfaces: Smooth, glabrous. Color, upper surface: Close to 138A. Color, lower surface: Close to 146B.

Inflorescence description:

*Flower arrangement/habit*.—Single rotate flowers arranged in terminal clusters; very freely flowering with numerous flower buds and flowers per plant; flowers face upright and outwardly.

*Fragrance*.—None detected.

*Natural flowering season*.—Plants flower naturally from the spring to autumn in Southern California; flowering continuous during this period.

*Flower longevity on the plant*.—About five to seven days; flowers persistent.

*Flower diameter*.—About 1.1 cm.

*Flower depth (height)*.—About 1 cm.

*Floral bracts*.—Quantity and arrangement: Two to four; opposite. Length: About 5 mm. Width: About 2 mm. Shape: Narrowly spatulate. Apex: Broadly acute to rounded. Base: Attenuate. Margin: Entire. Texture, upper and lower surfaces: Smooth, glabrous. Color: When opening and fully opened, upper surface: Close to NN155D. When opening and fully opened, lower surface: Close to NN155D. Petioles: Length: About 2 mm. Diameter: Less than 1 mm. Texture, upper and lower surfaces: Smooth, glabrous. Color, upper and lower surfaces: Close to 138C.

*Peduncles*.—Length: About 1.5 mm. Diameter: Less than 1 mm. Strength: Moderately strong. Texture: Smooth, glabrous. Color: Close to 138A.

*Cyathia*.—Quantity per flower: About two. Length: About 3.5 mm. Diameter: About 2.5 mm. Shape: Oval. Aspect: Upright. Color, immature: Close to 138A. Color, mature: Close to 137A.

*Nectaries*.—Nectary development has not been observed on plants of the new *Euphorbia*.

*Reproductive organs*.—Androecium: Quantity: About two to three stamens per cyathia. Filament length: About 1 mm. Filament color: Close to NN155D. Anther length: Less than 1 mm. Anther shape: Bilobed. Anther color: Close to 2B. Pollen amount: Scarce. Pollen color: Close to 2B. Gynoecium: Quantity: One per cyathia. Pistil length: About 3 mm. Style length: About 1 mm. Style color: Close to NN155D. Stigma shape: Branched. Stigma color: Close to NN155D. Ovary color: Close to 137D. Seeds and fruits: Seed and fruit development have not been observed on plants of the new *Euphorbia*.

Temperature tolerance: Plants of the new *Euphorbia* have been observed to have tolerate temperatures ranging from about 10° C. to about 40° C.

Pathogen & pest resistance: Plants of the new *Euphorbia* have not been observed to be resistant to pathogens and pests common to *Euphorbia* plants.

It is claimed:

1. A new and distinct *Euphorbia* plant named 'UNIEUP-1' as illustrated and described.

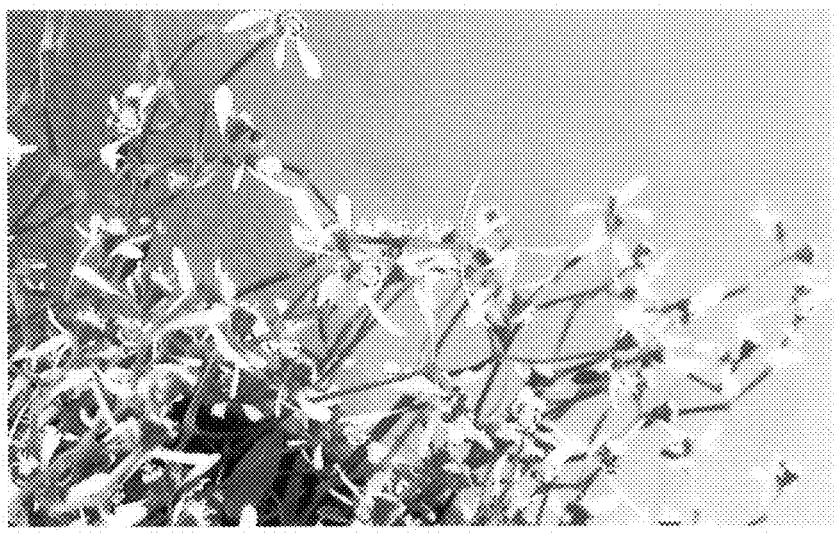
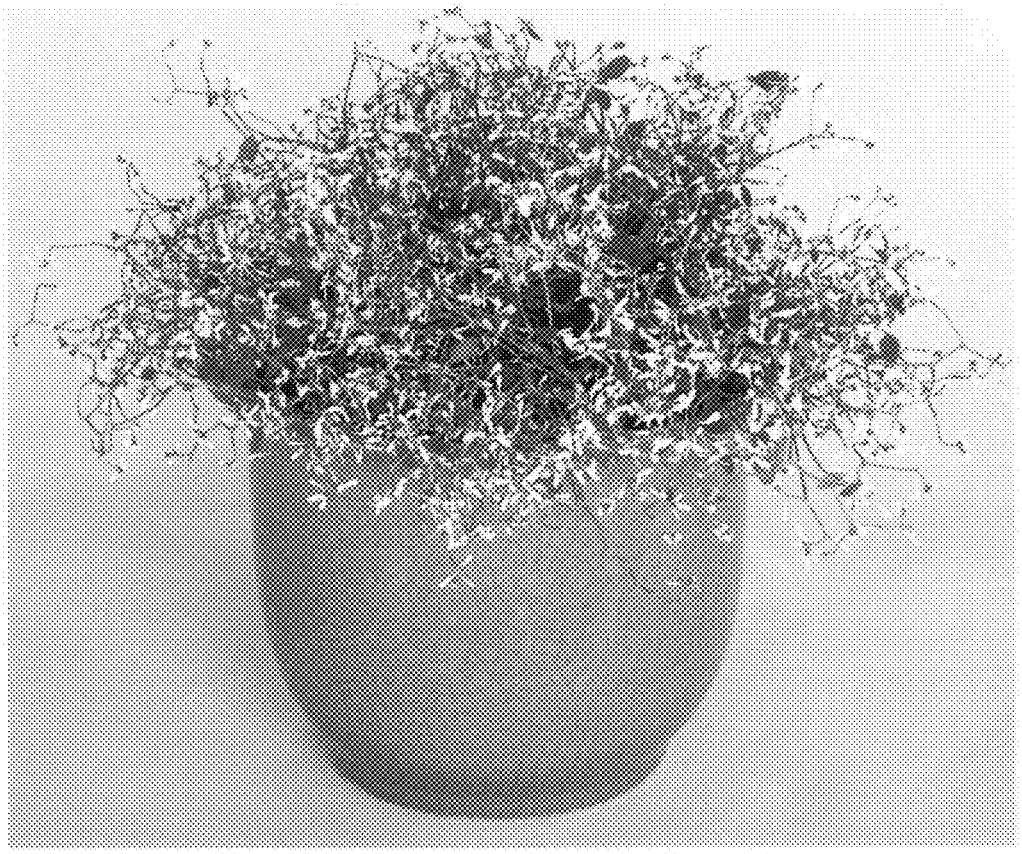

* * * * *